United States Patent [19]

Lontrade et al.

[11] Patent Number: 5,249,712
[45] Date of Patent: Oct. 5, 1993

[54] PACKAGING FOR ALTERING THE COMPOSITION OF A LIQUID

[75] Inventors: Jean-Pierre Lontrade; Henri Chibret, both of Clermont Ferrand; Gérard Schwadrohn, Nice, all of France

[73] Assignee: Transphyto S.A., Clermont Ferrand, France

[21] Appl. No.: 678,280
[22] PCT Filed: Oct. 26, 1989
[86] PCT No.: PCT/FR89/00559
§ 371 Date: Apr. 29, 1991
§ 102(e) Date: Apr. 29, 1991
[87] PCT Pub. No.: WO90/04547
PCT Pub. Date: May 3, 1990

[30] Foreign Application Priority Data

Oct. 28, 1988 [FR] France ............... 88 14211

[51] Int. Cl.5 .................................. B67D 5/58
[52] U.S. Cl. ..................... 222/189; 210/266; 210/475; 210/501; 222/129; 222/190; 222/212; 222/525
[58] Field of Search ........... 222/129, 145, 189, 190, 222/206, 207, 212, 215, 522, 523, 525, 559; 210/266, 475, 482, 501, 502.1

[56] References Cited

U.S. PATENT DOCUMENTS

| | | | |
|---|---|---|---|
| 2,761,833 | 9/1956 | Ward | 222/189 X |
| 3,189,223 | 6/1965 | Mackal | 222/189 X |
| 3,441,179 | 4/1969 | Ragan | 222/129 |
| 3,463,322 | 8/1969 | Gerarde | 222/189 X |
| 4,529,511 | 7/1985 | Breeden et al. | 210/266 X |
| 4,938,389 | 7/1990 | Rossi et al. | 222/189 |
| 4,947,986 | 8/1990 | Ballu | 222/145 X |
| 5,013,459 | 5/1991 | Gettings et al. | 210/501 X |
| 5,056,689 | 10/1991 | Heyl et al. | 222/190 X |

FOREIGN PATENT DOCUMENTS

| | | |
|---|---|---|
| 0077556 | 10/1982 | European Pat. Off. . |
| 0236033 | 9/1987 | European Pat. Off. . |
| 0357288 | 3/1990 | European Pat. Off. . |
| 889973 | 9/1953 | Fed. Rep. of Germany ...... 222/190 |
| 3419572 | 12/1984 | Fed. Rep. of Germany ...... 222/189 |
| 1367129 | 6/1964 | France . |
| 0042180 | 12/1979 | Japan .................... 210/501 |
| 8100842 | 4/1981 | World Int. Prop. O. ......... 222/189 |

Primary Examiner—Kevin P. Shaver
Attorney, Agent, or Firm—Millen, White, Zelano, & Branigan

[57] ABSTRACT

A package for a liquid which is purified includes a neck with a lock-chamber slidable therein. The lock-chamber includes a purifying substance through which the liquid passes when dispensed. At one end of the lock chamber, a plug is positioned to block passage of the liquid through the lock-chamber when the lock-chamber is projected from the neck and to allow passage of the liquid when the lock-chamber is pushed down into the neck.

9 Claims, 4 Drawing Sheets

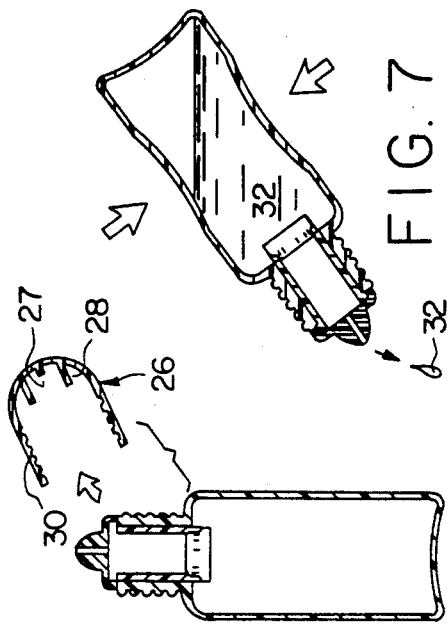
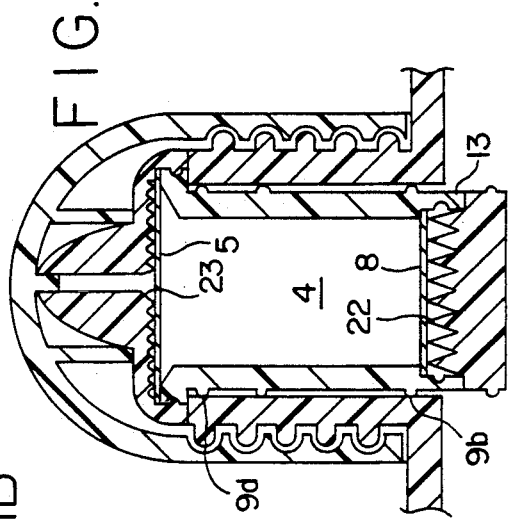
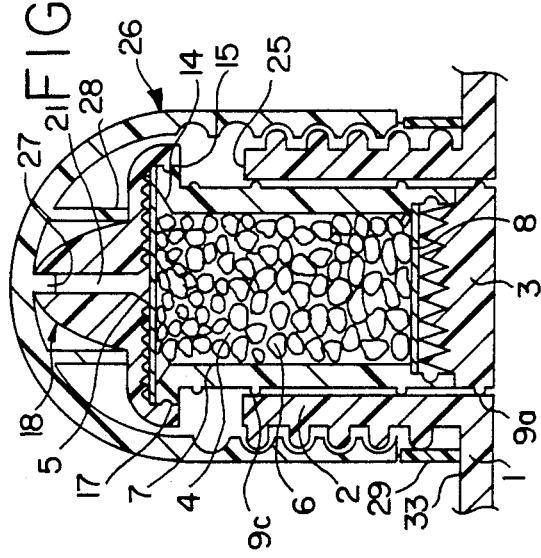
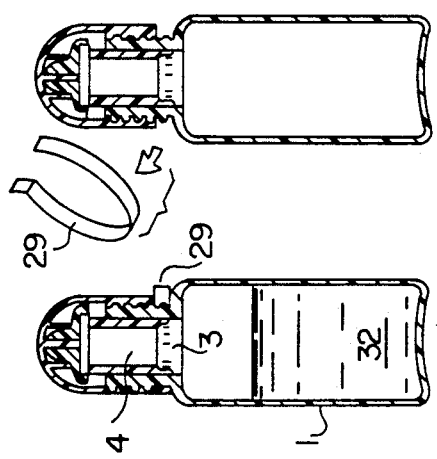

PACKAGING FOR ALTERING THE COMPOSITION OF A LIQUID

The present invention relates to the industry concerned with the packaging and purification of liquids, more particularly in containers provided with an incorporated obturator, and especially the physical or chemical modification of a liquid.

The invention finds a particularly advantageous application in the pharmaceutical industry, especially in regard to therapeutic products for local application as employed in ophthalmology, dermatology, gynecology as well as in cosmetology. The invention is of course also applicable, for example, in the field of bottles of household products or chemical products.

There exists a known type of container, especially of plastic material with elastically deformable walls and a neck containing an inseparable obturator which is movable at will between a closed position and an open position of the container, of the type provided in plug valves or slide valves.

It is sometimes necessary to modify the liquid delivered, in particular by extraction of an undesirable substance by passing through a filter element or purifying element which is external to the container or else by extemporaneous addition of a substance which is soluble in the liquid contained in the container, which is fairly common in the case of therapeutic solutions of lyophilizates and is usually carried out by confinement of the additional substance in a breakable envelope within the container until the moment of use.

The answers given to these packaging problems up to the present time are subject to practical disadvantages which arise in particular from the complexity of the elements to be assembled and on the other hand from the fragility of elements which are external to the container or in contact with the liquid prior to use. Moreover, it is necessary to design a specific package for each application, which limits production series and influences industrial costs.

SUMMARY OF THE INVENTION

One object of the invention is to provide a readily standardizable package for liquids which makes it possible to keep the liquid isolated from the exterior and from any additional substances or from filtering or purifying elements up to the moment of use, composed of elements which are simple to produce and to assemble in order to constitute a unitary package which is easy to handle, rugged and inexpensive.

Another object of the invention is to carry out extemporaneous purification of small fractional quantities which are withdrawn from a liquid within a container as it is being used.

For the preservation of such products during storage, in particular for products which are intended for a therapeutic application, it is often necessary and even legally compulsory to add preservatives dissolved in the stored liquid. In the majority of instances, however, these preservatives have undesirable effects after or during therapeutic application. It is thus often found to produce irritations which inhibit the action of scar-forming products or the like.

One is thus faced with a problem which is apparently difficult to solve : the need to keep a therapeutic solution in the sterile state during a suitable period of storage which involves the addition of a preservative and the need to apply the same sterile solution in the pure state and therefore without preservative. This problem is further complicated by the fact that the use of a package is fragmented in the majority of local therapeutic applications. Once the container has been opened, the liquid is in contact with the surrounding air and loses its sterility if it does not contain any preservative.

A common solution to this problem which is adopted at the present time consists in packaging the sterile liquids in containers corresponding in each case to an entire treatment, which may be completely purified prior to application subject, however, to the risk of a loss of sterility. It has also been proposed to protect the sterility of the contents of a container between successive fractional withdrawals by placing a sterilizing filter at the outlet of the container.

A filter of this type does in fact afford protection of sterility against external contamination of the non-delivered liquid which remains within the container but allows any preservative to remain in the delivered liquid, with all its disadvantages. Any (total) purification of the fraction of liquid delivered at the outlet of the container entails a risk of loss of sterility of the applied liquid and involves handling operations which are not convenient for the patient who is an occasional user.

The aim of the invention is to solve this problem and to make it possible to keep a fractionizable quantity of liquid containing a substance which is undesirable for use, especially a therapeutic liquid preservative, and to deliver this liquid at will in successive doses, in a sterile state and purified of the undesirable substance, without any particular handling operation.

In accordance with its principal feature, the invention is concerned with a package for a liquid to be purified, comprising a container having a neck which surrounds a lock-chamber for receiving at least one element for the treatment of the liquid when it is discharged from the container, as distinguished by the fact that said lock-chamber is rigidly fixed to an obturator or movable plug which is capable of displacement at least at the time of initial use between a storage position in which it isolates the interior of the container from the lock-chamber and a position of use in which it establishes a communication between the interior of the container and the interior of the lock-chamber, said obturator being intended to remain rigidly fixed to said lock-chamber which has a constant internal volume.

The lock-chamber advantageously contains a purifying substance which is insoluble in the liquid retained between an upstream filter element and a downstream filter element.

The mechanical construction and the structure of the package enable this latter to receive in the lock-chamber a treatment element or element for modifying the liquid which is in contact with the liquid only at the moment of discharge of this latter.

There is thus provided a lock-chamber/obturator unit which, at the time of storage of the container prior to use, makes it possible for a modification element contained in the lock-chamber to be completely isolated from the liquid contained in the container, with the result that the container can thus be stored in any position without interfering with the preservation of the liquid product contained therein.

Furthermore, the fact that the lock-chamber is limited by a filter at each end considerably increases the number of possible modes of treatment of the liquid at the time of use and permits the possibility of employing this type of package in many different applications without any need to modify its structure.

Arrangements may thus advantageously be made to ensure that the lock-chamber contains a purifying substance or element for modification of the liquid, that an upstream filter element or first filter element has the effect of retaining a first type of particles before the liquid reaches the purifying substance and that a downstream filter element or second filter element retains a second type of particles prior to discharge of the liquid to the exterior, an additional function of the two filter elements being that of retaining the purifying substance within the lock-chamber.

Moreover, as will be explained hereinafter, the fact that the obturator remains rigidly fixed to the lock-chamber irrespective of the position of the unit makes it possible, while retaining an identical package structure, to employ the package for applications in which it is desired to isolate the interior of the lock-chamber from the interior of the container after each period of use and/or for applications in which it is desired to be able to mix a product with the entire quantity of liquid prior to initial use.

In addition, the structure of this package permits a constant internal volume of the lock-chamber irrespective of the position of storage or of utilization of the package, with the result that the useful volume of the lock-chamber is identical with its internal volume, thus achieving a reduction in overall size of the complete assembly.

The lock-chamber can advantageously contain a purifying substance which is insoluble in the liquid. The downstream filter element can advantageously be a bacteriological filter.

In an application to a therapeutic solution in which the undesirable substance, only at the moment of use, is a product of local application of the group comprising eye lotions, nasal solutions, dermatological lotions and in a general manner the products to be applied in contact with mucous membranes or at their periphery, the lock-chamber advantageously contains a substance having the effect of removing a preservative contained in the liquid to be purified.

The permeability of the filter elements and especially of the upstream filter element is advantageously such that a predetermined minimum pressure difference (example: manual pressure on the walls of a flexible container) is necessary for the passage of the liquid in order to prevent contact in the event of sudden jerks between periods of use.

The package in accordance with the invention advantageously comprises means for varying the internal volume of the container. This makes it possible, for example, by producing action on elastically deformable walls, to discharge the liquid contained therein.

In a particularly advantageous embodiment, the means for varying the internal volume of the container comprise at least one movable wall of the container, for example the bottom end-wall, in the same manner as a syringe so as to reduce the internal volume of the container as the liquid contained therein is being discharged. This makes it possible to guard the liquid against any possible contamination by air during successive periods of use inasmuch as the admission of air into the container is avoided by the fact that this latter does not replace the discharged liquid by air.

In an advantageous embodiment, the lock-chamber and the plug form a unit assembly having a tubular body, the body being provided with at least one duct for the flow of liquid through the plug and an end-wall which closes these flow means by fluid-tight cooperation, especially by means of a fluid-tight nozzle, with the neck of the container prior to initial use.

The lock-chamber/plug unit is capable of sliding within the neck of the container and can be brought at will from the storage position in which said unit is isolated from the interior of the container which it seals-off to the position of use in which the interior of the container is put into communication with the exterior via said unit in order to fill the container with liquid or to deliver said liquid.

In practice, the lock-chamber/plug unit is advantageously constituted by a tubular body of revolution, the end of said body which is intended to communicate with the exterior being provided with an internal flared-out portion in a terminal annular flange, the external radial face of which forms a fluid-tight annular support for the periphery of said downstream filter element and said unit advantageously comprises a delivery nozzle having an internal annular shoulder which applies the periphery of the downstream filter element against the annular bearing shoulder of the annular flange and having means for causing the liquid to flow between the external face of the downstream filter element and an axial delivery duct of the nozzle.

In a package of this type, good closure of the container in the storage position and effective freeing of the liquid flow passages in the position of use are facilitated if the length of the lock-chamber/plug unit is greater than that of the container neck in which the unit slides, the plug and the section of the tubular body which has the same diameter being provided with annular sealing lips or beads in the neck in the storage position and in the position of use. The annular flange forms a stop on the edge of the container neck in order to limit the extent of downward travel of the lock-chamber/plug unit towards the position of use in which at least one lateral opening of the plug is freed from the neck whereas it is enclosed and isolated in fluid-tight manner within the neck in the storage position.

Isolation of the exterior of the lock-chamber/plug unit in the storage position as well as in the position of use outside periods of use, at the same time as the operation which consists in putting in the position of use, are advantageously obtained by means of a cap which is screwed onto the exterior of the neck and which has an axial stud for shutting-off the delivery duct of the nozzle as well as an internal annular extension applied against the external face of the nozzle in order to thrust this latter by hand in the downward direction within the neck towards the position of use, the cap being provided with a breakable safety ring forming an extension of its skirt and applied against the neck base of the container so that after initial use, the cap and the nozzle are no longer capable of causing the displacement of the lock-chamber/plug unit.

In a preferred embodiment of the invention, the lock-chamber/plug unit is advantageously formed in a single piece by said tubular body and this latter is provided at the end which is intended to communicate with the interior of the container with a chamber which receives a product to be mixed with the liquid at the time of initial setting in the position of use and which discharges through a first lateral opening into the periphery of said plug and through a second opening into said lock-chamber opposite to said upstream filter element, said reception chamber being advantageously isolated from the interior of the container in the storage position and in communication with this latter in the position of use, said product being poured into said container at the time of initial setting in the position of use.

This structure makes it possible in a particularly advantageous manner to combine the use of a treatment or modification element which is not soluble in the liquid and contained in the lock-chamber and which purifies a dose of liquid at each use, with the use of a product which is soluble in the liquid and especially a lyophilizate which is contained in the chamber formed in the plug and which is poured into the container at the time of initial setting in the position of use.

The tubular body advantageously has a fluid-tight annular shoulder for supporting said upstream filter element at the periphery which constitutes the separation between the lock-chamber and the plug. It is thus possible without changing the overall size of the lock-chamber/plug unit to modify the respective volumes of the lock-chamber and of the chamber as a function of the desired application and of the modification elements to be employed, by means of a different longitudinal positioning of the annular shoulder which supports the first filter element.

Moreover, by virtue of the single-piece constructional design of the lock-chamber/plug unit, the invention can be readily applied to packages which are manufactured, filled and closed without any interruption of continuity, for example in accordance with a method of sterile extemporaneous packaging known by the trade name "Bottle-Pack".

In accordance with another embodiment of the invention, the lock-chamber/plug unit can be practically constituted by a tubular body of revolution provided at that end which is intended to communicate with the interior of the container with an internal annular shoulder for supporting a first filter element at the periphery and fluid-tight snap-action engagement means for a plug having the same external diameter as the tubular body, a peripheral edge of which applies the first filter element against the annular shoulder for supporting the tubular body and in which are cut radial channels for the free flow of liquid, said channels being intended to open beneath the first filter element on the side nearest the container.

In order to provide a good support for the filter elements and good circulation of liquid, it is an advantage to ensure that the faces of the plug and of the nozzle opposite to the filter elements, apart from the periphery, have rough surface excrescences which support the faces of the filter elements and form between them intercommunicating channels for the circulation of liquid.

In another embodiment of the invention in which it is desired to isolate the interior of the lock-chamber from the interior of the container between the periods of use in order to preserve the liquid irrespective of the position in which the container is stored, the lock-chamber/obturator unit is advantageously displaceable at will between said storage position and said position of use.

To this end, steps can advantageously be taken to ensure that the nozzle has means for gripping by the user and for imparting a movement of translation to the lock-chamber/plug unit.

In an alternative embodiment, the lock-chamber/plug unit is advantageously associated with a rotational closure device within an inverted neck of the container, the plug being provided with a bottom end-wall with open portions and an axial stud latched in rotation in a wall which partially shuts-off the internal end of the inverted neck.

In the case of applications in which the liquid of the container consists of an emulsion and especially if the active product to be applied is only an oily compound of this emulsion as may be the case for example when the conditions of preservation of an oily compound require that it should be mixed with an aqueous compound, it is particularly advantageous to ensure that the upstream filter element is permeable to all the constituents of the liquid and that the downstream filter element is selectively permeable to the oily compound while retaining the aqueous compound in the lock-chamber.

Conversely, should it be desired to retain the oily compound, it is an advantage to ensure that the upstream filter element is selectively permeable to the aqueous compound or permeable to all the constituents of the liquid and that the downstream filter element is selectively permeable to the aqueous compound alone, the preservative which may be contained in the aqueous compound being trapped within the lock-chamber.

BRIEF DESCRIPTION OF THE DRAWINGS

There will now be described in greater detail a particular embodiment of the invention which will serve to gain a better understanding of its essential features and advantages although it should be made clear that this embodiment is chosen by way of example without any limitation being implied. In this description, reference is made to the accompanying drawings, in which:

FIG. 1A is a cross-sectional view of the body wall of the lock chamber engaging the container neck;

FIG. 1B is a schematic view in elevation and in axial cross-section showing the lock-chamber/plug unit of a package in accordance with the invention, said unit being inserted in the neck of a container and covered with a cap in the storage position;

FIG. 2 is a view which is similar to that of FIG. 1B and showing the same lock-chamber/plug unit in the position of use;

FIG. 6A to 6D and 6 is a synoptic series of diagrams showing the configuration of the package of FIGS. 1B to 5 in the different stages from storage to delivery of the liquid;

DETAILED DESCRIPTION

Figure 5:
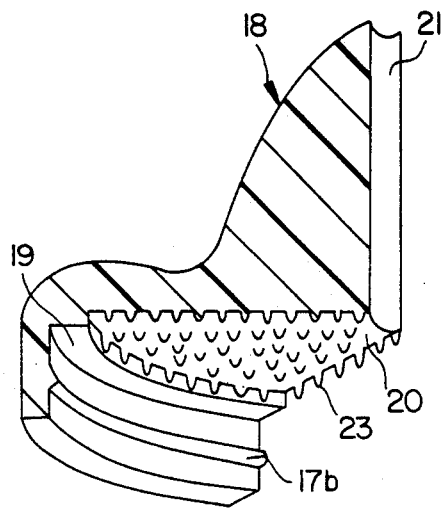
FIG. 5 is a partial schematic view in perspective and in axial cross-section showing the distributor nozzle of the lock-chamber/plug unit of FIGS. 1B and 2.
Figure 4:
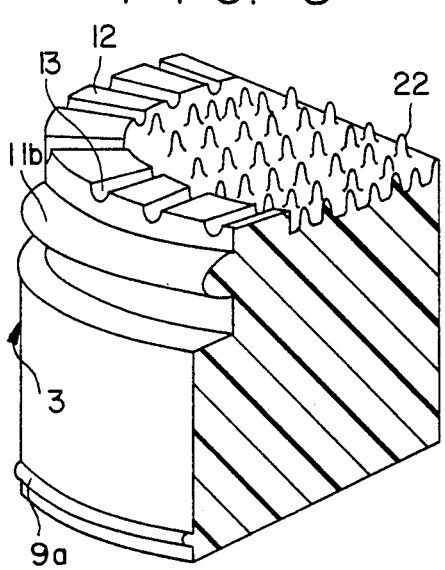
FIG. 4 is a partial schematic view in perspective and in axial cross-section showing the plug of the body/plug assembly of FIG. 3.
Figure 3:
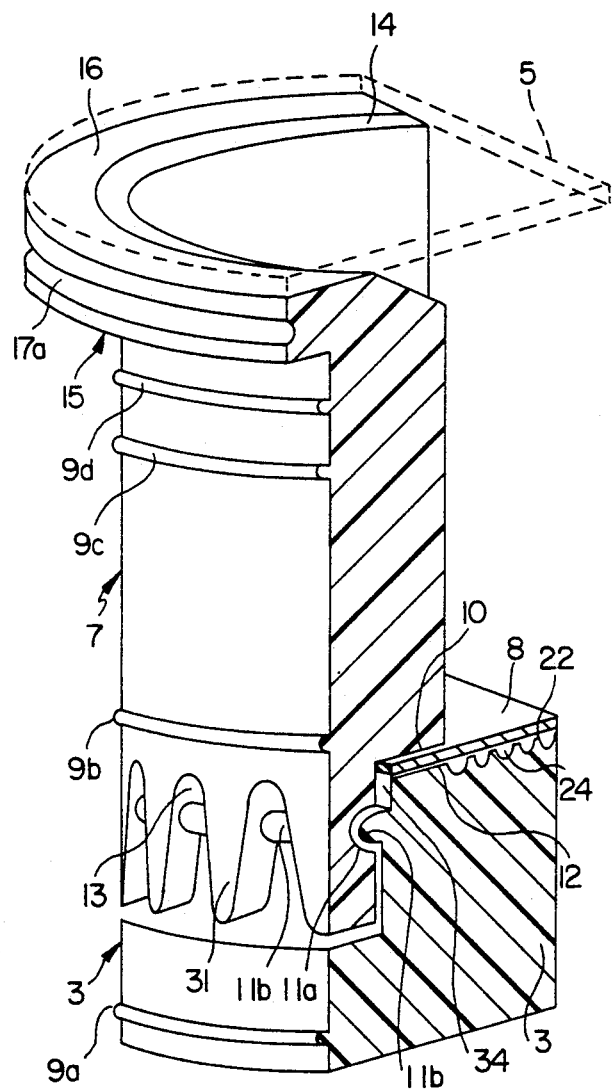
FIG. 3 is a partial schematic view in perspective and in axial cross-section showing the body/plug assembly of the lock-chamber/plug unit of FIGS. 1B and 2.

The package shown in these drawings essentially comprises a container 1, namely in this instance a bottle of polyethylene having elastically terminating in a plug 3 at the end nearest the container 1 and in a delivery nozzle 18 at the other end is inserted in the neck 2 of said container in an axial sliding movement. A cap 26 which covers the unit is screwed on the exterior of the neck 2.

The lock-chamber 4 is constituted by a tubular body 7 of revolution, the crenellated base 31 of which is provided internally with an annular peripheral bearing shoulder 10 for a first filter element or upstream filter element 8 which may be constituted by a perforated membrane, a woven fabric element or a sintered plate, as well as a snap-action engagement groove 11a for the plug 3.

The plug 3 has the same external diameter as the tubular body 7 and forms an extension of this latter. Its end face is full whilst its opposite face, namely the face located opposite to the first filter element 8, has an annular peripheral edge 12 located opposite to the annular shoulder 10 of the body 7. Radial channels 13 cut in said peripheral edge open externally opposite to the crenellated recesses 31 of the body 7 and internally into a set-back axial face studded with villosities 22. Intercommunicating channels 24 formed between said villosities ensure that the liquid flows freely beneath the first filter element from or towards the radial channels 13. The crenellated edge 12 of the plug has an external diameter which is slightly smaller than the internal diameter of the crenellated recesses 31 so as to form a peripheral collector duct 34 of the channels 13.

The periphery of the first filter element 8 is thus maintained applied in fluid-tight manner against the annular shoulder 10 of the body 7 by means of the peripheral edge 12 of the plug 3 which is snap-actingly engaged by means of a lateral peripheral rib 11b in the groove 11a at the end of the body 7. Moreover, the entire remaining portion of its surface on the side nearest the container 1 is held in position by the villosities 22 of the plug 3.

At the end remote from the plug 3, the body 7 terminates internally in a flared-out portion 14 and externally in an annular flange 15, the external radial face 16 of which forms a fluid-tight annular support for the periphery of a second filter element or downstream filter element 5 which may be constituted by a microporous membrane or a bacteriological filter. The external lateral face of the annular flange 15 has a circular groove 17a which cooperates with an internal peripheral rib 17b of the pipe of the delivery nozzle 18 in order to ensure snap-on engagement of this latter.

The nozzle 18 has an axial delivery duct 21, one end of which opens to the exterior and the other end of which has its opening at the center of a face studded with villosities 23 between which are formed interconnecting channels 20. Said face is surrounded by a peripheral annular shoulder 19 forming a fluid-tight annular support for the periphery of the second filter element 5 located opposite to the external radial face 16 of the body 7.

The second filter element 5 is thus maintained in fluid-tight manner, by means of its periphery, between the body 7 and the nozzle 18 which are snap-fastened to each other. In addition, said element is supported by the villosities 23 over the remainder of its surface and the liquid can flow freely through the element from or towards the delivery duct 21.

Between the first filter element 8, the second filter element 5 and the internal wall of the body 7, there is delimited an enclosure forming a lock-chamber 4 which may be filled either partially or completely with a soluble or insoluble substance for modifying the liquid 32 to be delivered. The substance considered may be a salt or a lyophilizate or a purifying substance.

Fluid-tightness of the unit consisting of lock-chamber 4 and plug 3 within the neck is ensured at each end of neck 2 in the storage position (FIG. 1B) by means of peripheral annular ribs 9a of the plug 3 and 9c of the body 7 and in the position of use (FIG. 2) by means of peripheral annular ribs 9b and 9d of the body 7.

The length of the unit consisting of lock-chamber 4 and plug 3 is such that, in the storage position (FIG. 1B), the base of the plug 3 practically does not project beyond the inner edge of the neck 2 within the container 1 whereas in the position of use (FIG. 2), the plug 3 penetrates into the interior of the container 1 to a sufficient depth to ensure that the channels 13 open freely beneath the inner edge of the neck 2 whereas the bottom radial edge of the annular flange 15 is abuttingly applied on the outer edge 25 of the container neck 2.

In a position of use (FIG. 2), the peripheral edge of the nozzle 18 is applied against the outer edge 25 of the container neck without any interruption of continuity, which thus prevents any possibility of gripping and inopportunely returning the lock-chamber/plug unit to the storage position (FIG. 1B). By way of alternative, the edge of the nozzle could be fitted in an annular recess in the edge of the neck.

The cap 26 is screwed onto the threaded outer edge of the neck 2 of the container 1. Its internally threaded skirt has an extension in the form of a breakable guarantee ring 29 which can readily be torn-off for initial use of the package. During storage, said guarantee ring 29 is normally in abutment with the neck base 33 of the container (FIG. 1B) in order to prevent any untimely screwing towards the position of use (FIG. 2). An axial stud 27 seals off the delivery duct 21 of the nozzle 18 whilst an internal annular extension 28 bears on the external face of the nozzle 18. When the guarantee ring 29 has been torn-off, the cap 26 is screwed-down by hand and produces the downward displacement of the unit consisting of nozzle 18, lock-chamber 4 and plug 3 until the annular flange 15 abuts against the edge 25 of the neck, thus determining the position of use (FIG. 2) whilst the delivery duct 21 remains closed by the stud 27. It is then possible to unscrew and remove the cap 26 from the package without displacing the unit consisting of nozzle 18, lock-chamber 4 and plug 3.

The liquid 32 within the container 1 can then be delivered by pressing the walls in order to force it through the lock-chamber 4 and its filter elements 8 and 5 and in order to deliver it through the duct 21 of the nozzle 18.

In the event of fractional deliveries of liquid, the cap 26 is replaced in position, thus isolating the lock-chamber 4 and consequently the container 1 from the exterior. The air sucked-in by elastic return of the container walls is filtered by the filter elements 5 and 8 and also by the substance 6 which may be enclosed within the lock-chamber, and protects the remaining liquid 32 from any pollution, as well as the interior of the lock-chamber.

Figure 8:
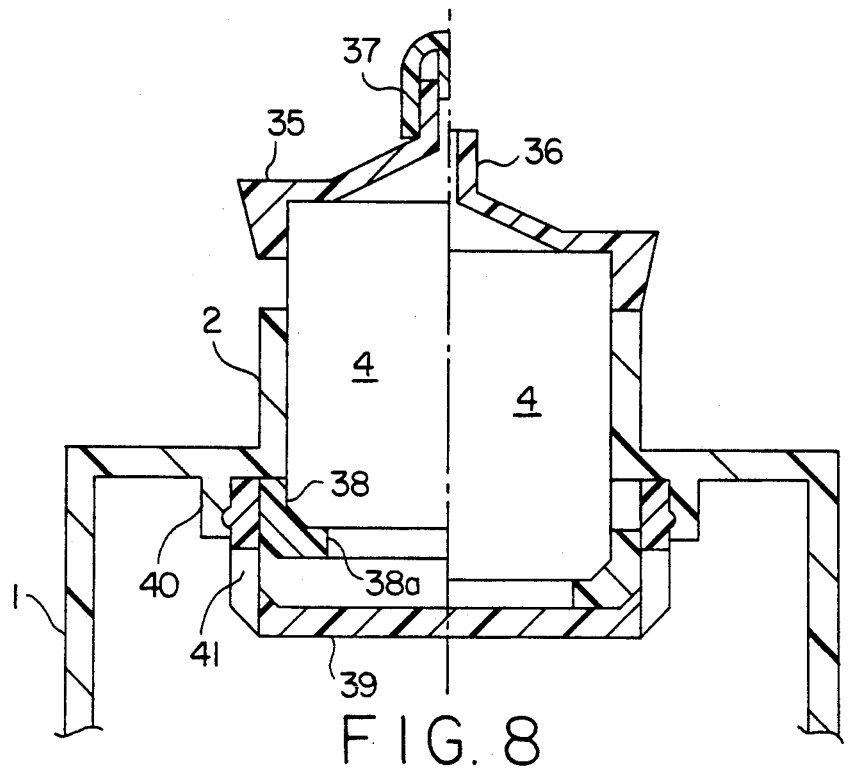
FIGS. 8 and 9 are schematic views in elevation and in axial cross-section showing two alternative forms of construction which make it possible to isolate the lock-chamber from the interior of the container between each period of use.
Figure 9:
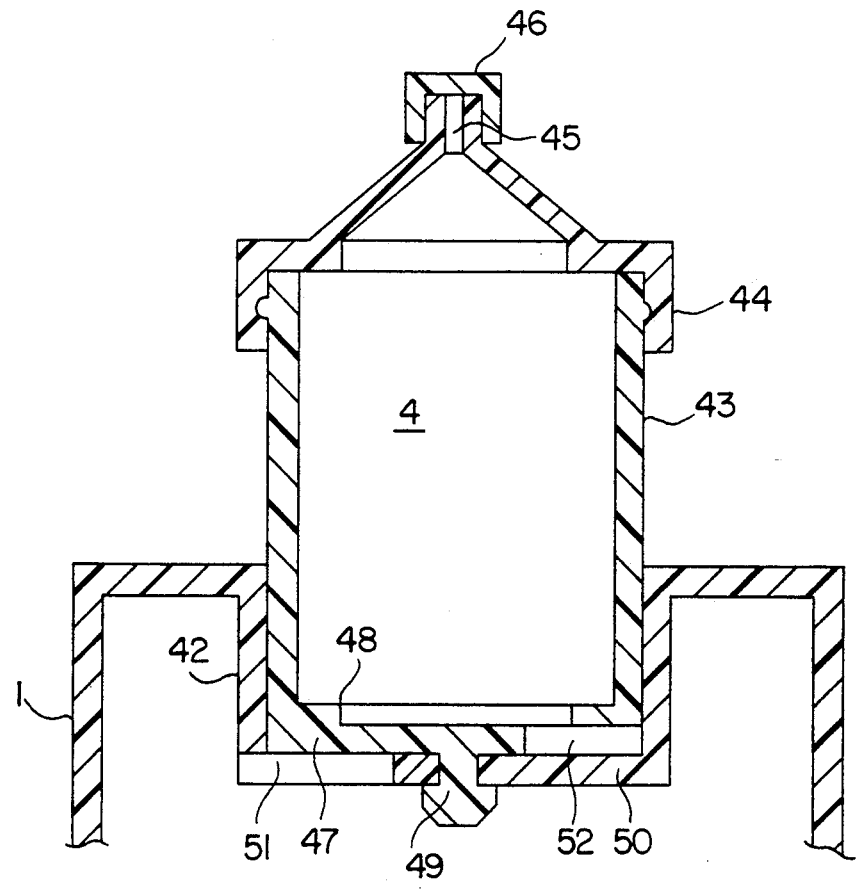

The alternative embodiments shown in FIGS. 8 and 9 relate to a package primarily intended for applications in which it is desired that the interior of the lock-chamber 4 should be isolated from the interior of the container 1 between different periods of use irrespective of the position in which the package is stored.

The figures illustrating these alternative embodiments are schematic and the filter elements are not shown in these figures for reasons of clarity.

The package of FIG. 8 comprises a lock-chamber 4 associated with a closure device with axial translational motion within the smooth-walled neck 2 of a container 1. At its outer end, the lock-chamber 4 is covered by a welded, bonded or screwed conical end-piece 35 terminating in an axial nozzle 36 which can be sealed-off at will by means of a conventional cap 37, said end-piece being such as to constitute gripping means enabling a user to impart a movement of translation to the unit consisting of lock-chamber 4 and plug 38. The inner end of the lock-chamber 4 constituted by the plug 38 is slidably mounted in a blind end-piece 39 snap-fastened in an internal annular flange 40 derived from the neck base of the container 1 and provided with lateral openings 41 in the vicinity of the blind end-wall. The plug 38 is provided at its outer end with an externally-fitted frusto-conical annular flange 38a whilst the blind-end wall of the end-piece 39 is provided internally with a conicity which is complementary to that of the flange 38a of the plug 38. The respective dimensions of the plug 38 within the blind end-piece 39 and their displacement are such that, when the unit consisting of end-piece 35, lock-chamber 4 and plug 38 is moved downwards to the full extent within the blind end-piece 39 and the base of the end-piece 35 is abuttingly applied against the end of the neck 2, the plug 38 shuts-off the openings 41 and isolates the interior of the container 1 from the lock-chamber 4 and from the exterior, as shown in the right-hand half-view of FIG. 8.

On the other hand, when the end-piece assembly 35 is pulled outwards and the plug 38 is abuttingly applied against the base of the neck 2, the openings 41 are freed, the interior of the container communicates freely with the lock-chamber 4 and the nozzle 36 opens to the exterior after removal of the cap 37, as shown in the left-hand half-view of FIG. 8.

FIG. 9 illustrates another alternative embodiment of the package in accordance with the invention and of the obturator in which a lock-chamber 4 is associated with a rotational closure device within the inverted neck 42 of a container 1. The lock-chamber 4 is limited by a body 43 closed by a snap-fastened conical end-piece 44 terminating in an axial delivery nozzle 45 which can be closed at will by means of a conventional cap 46. The plug 47 is provided with open portions and with an internal annular shoulder 48 on which is applied the peripheral edge of an upstream filter element, the bottom central face of which is thus freed from the end-wall of the plug 47.

An axial stud 49 extending from the plug 47 is latched in rotation in a wall 50 which partly shuts-off the inner end of the inverted neck 42. The wall 50 and the plug 47 of the body 43 are provided with identical openings 51, 52 respectively in circular arcs of less than 180 degrees (90 degrees, for example) which can be moved at will by rotation of the body 43, either opposite to each other so as to cause the interior of the container 1 to communicate with the lock-chamber 4 and with the exterior via the nozzle 45 after removing the cap 46, or each and respectively opposite to the plug 47 of the body 43 and to the wall 50 of the inverted neck 42 in order to isolate the interior of the container 1 from the lock-chamber 4 and from the exterior, as shown in FIG. 9.

Irrespective of the mode of utilization of the lock-chambers 4, it is imperative to ensure that the assemblies have seals such that the liquid cannot flow in any direction other than through the lock-chamber. This can be achieved in accordance with conventional practice by means of ribbed lips, beaded edges or elastic seals.

Figure 10:
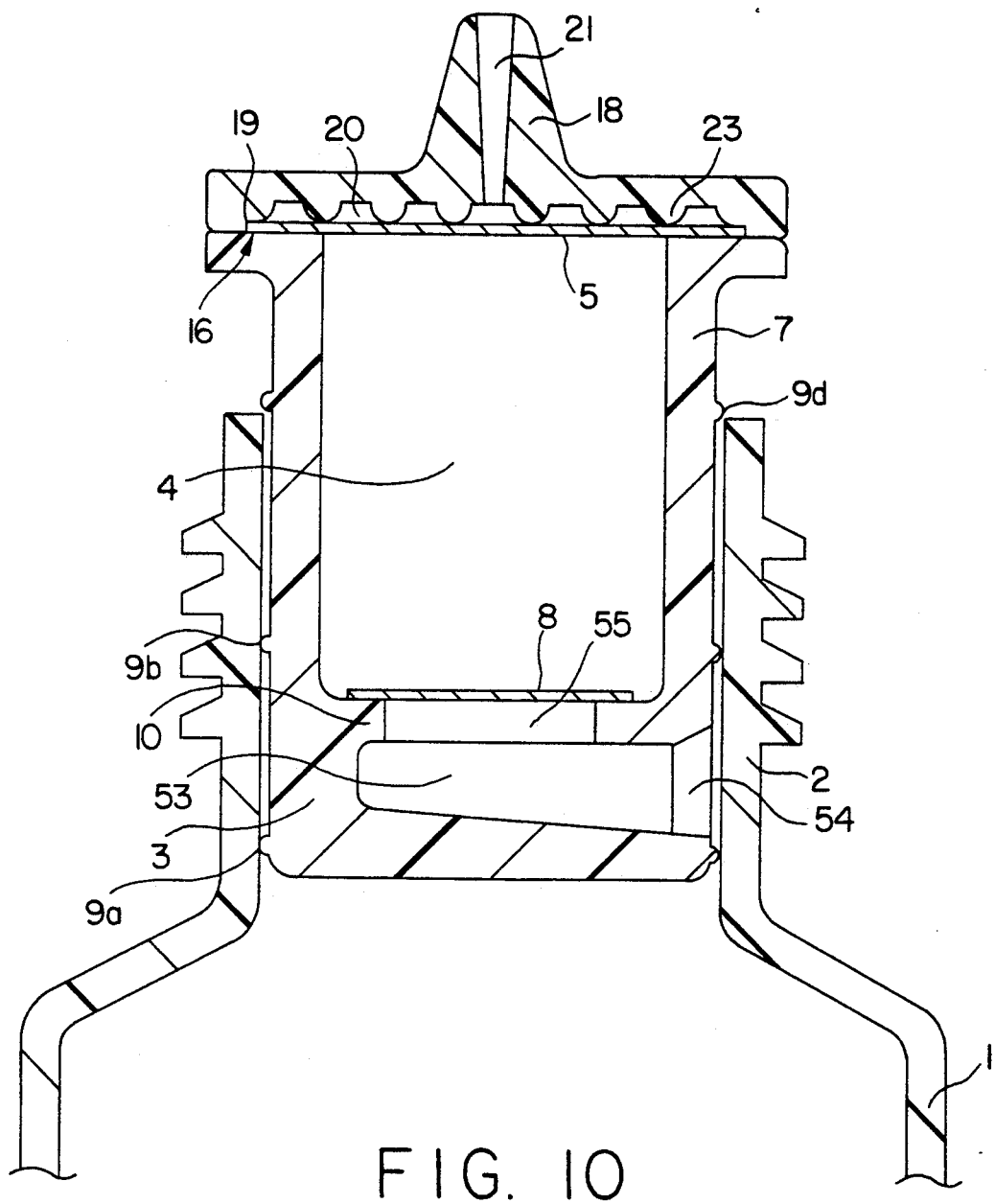
FIG. 10 is a schematic view in elevation and in axial cross-section showing a form of construction of the lock-chamber/plug unit which makes it possible to pour a product into the container prior to initial use.

FIG. 10 illustrates a preferred embodiment of the package in accordance with the invention in which the unit consisting of lock-chamber 4 and plug 3 is formed in a single piece by a tubular body 7.

The plug 3 constituting that end of the body 7 which is intended to communicate with the interior of the container 1 has a chamber 53 for receiving a product to be mixed with the liquid within the container 1 during initial setting of the package in the position of use. This chamber 53 has a first lateral opening 54 in the periphery of the body 7 at the level of the plug 3 between two peripheral annular ribs 9a, 9b of the body 7, the rib 9a being applied in fluid-tight manner against the internal periphery of the neck 2 of the container 1 in the storage position of the unit consisting of lock-chamber 4 and plug 3 and the rib 9b being applied in fluid-tight manner against the internal periphery of the neck 2, irrespective of the position of the unit comprising lock-chamber 4 and plug 3.

An additional peripheral annular rib 9d of the body 7 is provided for perfecting fluid-tightness in the position of use and for ensuring that fluid-tightness is achieved irrespective of the position of use or of storage, by means of two ribs.

A second opening 55 of the chamber 53 provides an access to the lock-chamber 4 opposite to an upstream filter element 8. Once the product contained in the chamber 53 has been mixed with the liquid, this second opening serves to establish a communication between the interior of the container 1 and the lock-chamber 4 by means of the chamber 53 which accordingly performs the function of the channels 13 of the embodiment shown in FIGS. 1A, 1B to 5.

The package illustrated in FIG. 10 is also provided with a nozzle 18 having an axial delivery duct 21, one end of which opens to the exterior whilst the other end has its opening at the center of a face studded with villosities 23 forming intercommunicating channels 20. Said face is surrounded by a peripheral annular shoulder 19 which forms a fluid-tight annular support for the periphery of a downstream filter element 5 opposite to the external radial face 16 of the body 7.

The separation between the lock-chamber 4 and the plug 3 is constituted by a fluid-tight annular shoulder 10 which supports the upstream filter element 8 at the periphery and which forms the opening 55.

A cap which is similar to that described with reference to FIGS. 1A, 1B to 5 and which performs the same function is provided for covering the entire assembly.

All the elements of the package can be readily formed by molding identical or different plastic materials or else can be made of various machined materials.

The invention is naturally not limited in any sense to the particular features specified in the foregoing or to the details of the particular embodiment which has been chosen in order to illustrate the invention. Consideration can be given to all kinds of variants of the particular embodiment which has been described by way of example and of its constituent elements without thereby departing from the scope of the invention. This invention accordingly includes all the means constituting technical equivalents of the means described as well as their combinations.

We claim:

1. A package in the form of a container (1) for storing and dispensing a liquid to be purified, the container (1) defining an interior for containing the liquid, the container comprising:
   a neck (2) communicating with the interior of the container at a junction between the neck and the interior;
   a lock-chamber (4) received within the neck, the lock chamber (4) having opposed inlet and outlet ends and treating material therein for treating the liquid to be purified as the liquid passes therethrough upon being dispensed from the container;
   a plug (3) fixed to the lock chamber (4) and being moveable therewith between a storage position and a dispsening position;
   means (9a) engageable between the plug (3) and neck (3) for blocking liquid in the interior of the container (1) from contacting the treating material when the plug is in the storage position and for allowing contact between the liquid and treating material when the plug (3) is in position during which liquid is dispensed; and
   means (8) associated with the lock chamber (4) for preventing the treating material from flowing from the lock chamber (4) into the interior of the container (1) when the plug (3) is in the dispensing position.

2. The package in accordance with claim 1, wherein the treating material comprises a purifying substance (6) which is insoluble in the liquid, the purifying substance being retained between an upstream filter element (8) and a downstream filter element (5) positioned at said inlet and outlet ends, respectively, of the lock-chamber.

3. The package in accordance with claim 2, wherein the liquid to be purified contains a preservative and wherein the purifying substance is capable of removing the preservative.

4. The package in accordance with claim 2, wherein the downstream filter element (5) is a bacteriological filter.

5. The package in accordance with claim 2, wherein the filter elements (5, 8) include means which allow the liquid to be purified to pass through only with a predetermined minimum pressure difference.

6. The package in accordance with claim 1, wherein the container (1) has deformable walls which varies the internal volume of the container (1) when deformed.

7. The package in accordance with claim 6, wherein the deformable walls are elastic.

8. The package in accordance with claim 1, wherein at least one wall of the container (1) is movable so as to reduce its volume to permit the liquid container therein to be discharged.

9. The package in accordance with claim 1, wherein siad lock-chamber (4) and movable plug (3) constitute a unit displaceable by a user between said storage position and said dispensing position.

* * * * *